United States Patent
Boese et al.

(10) Patent No.: US 8,094,773 B2
(45) Date of Patent: Jan. 10, 2012

(54) METHOD AND DEVICE FOR GENERATING A THREE-DIMENSIONAL X-RAY IMAGING

(75) Inventors: Jan Boese, Eckental (DE); Frank Dennerlein, Forchheim (DE); Benno Heigl, Coburg (DE); Holger Kunze, Bubenreuth (DE); Michael Maschke, Lonnerstadt (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 12/890,779

(22) Filed: Sep. 27, 2010

(65) Prior Publication Data

US 2011/0075794 A1    Mar. 31, 2011

(30) Foreign Application Priority Data

Sep. 29, 2009   (DE) .................... 10 2009 043 421

(51) Int. Cl.
*A61B 6/00* (2006.01)
(52) U.S. Cl. .................... 378/9; 378/4; 378/21
(58) Field of Classification Search ........... 378/9, 22–26
See application file for complete search history.

(56) References Cited

U.S. PATENT DOCUMENTS

| | | | |
|---|---|---|---|
| 4,246,483 A * | 1/1981 | Weiss et al. ................ 378/23 |
| 4,439,866 A | 3/1984 | Ishida et al. |
| 4,516,252 A * | 5/1985 | Linde et al. ................ 378/23 |
| 4,924,485 A | 5/1990 | Hoeberling |
| 5,572,567 A | 11/1996 | Bleser et al. |
| 6,292,531 B1 * | 9/2001 | Hsieh ..................... 378/37 |
| 6,553,096 B1 | 4/2003 | Lu et al. |
| 7,359,484 B2 | 4/2008 | Lu et al. |
| 7,396,162 B1 * | 7/2008 | Edic et al. ............... 378/207 |
| 7,567,647 B1 * | 7/2009 | Maltz ..................... 378/21 |
| 2002/0006184 A1 | 1/2002 | Katoh et al. |
| 2003/0194121 A1 * | 10/2003 | Eberhard et al. ........... 382/132 |
| 2005/0133706 A1 * | 6/2005 | Eberhard et al. ........... 250/234 |
| 2005/0135558 A1 * | 6/2005 | Claus et al. .............. 378/42 |
| 2005/0226375 A1 * | 10/2005 | Eberhard et al. ........... 378/62 |
| 2006/0133564 A1 * | 6/2006 | Langan et al. ............. 378/8 |
| 2007/0025509 A1 | 2/2007 | Bani-Hashemi et al. |
| 2007/0053489 A1 * | 3/2007 | Lu et al. ................. 378/62 |
| 2009/0022264 A1 | 1/2009 | Lalush et al. |

FOREIGN PATENT DOCUMENTS

DE    10 2007 037 996 A1    2/2009

OTHER PUBLICATIONS

Xintek, Inc. Nanotechnology Innovations, Xintek's Field Emission X-Ray Technology, Retrieved Jul. 7, 2009 http://www.xintek.com/products/materials/feg.htm, Others.
Maltz, et al., "Fixed gantry tomosynthesis system for radiation therapy image guidance based on a multiple source x-ray tube with carbon nonotube cathodes", Medical Physics, vol. 36, No. 5, May 2009, © 2009 Medical Association Physics Medical, pp. 1624-1636, Others.

* cited by examiner

Primary Examiner — Edward Glick
Assistant Examiner — Alexander H Taningco

(57) ABSTRACT

A method is provided for quickly and simply generating a three-dimensional tomographic x-ray imaging. Tomosynthetic projection images are recorded from different recording angles along a tomosynthetic scanning path and three-dimensional image data is reconstructed from the tomosynthetic projection images. The tomosynthetic projection images are recorded by a tomosynthetic x-ray device with a plurality of x-ray sources arranged on a holder at a distance from one another. Each projection image is recorded by a different x-ray source being fixed in one place during recording the tomosynthetic projection images.

14 Claims, 2 Drawing Sheets

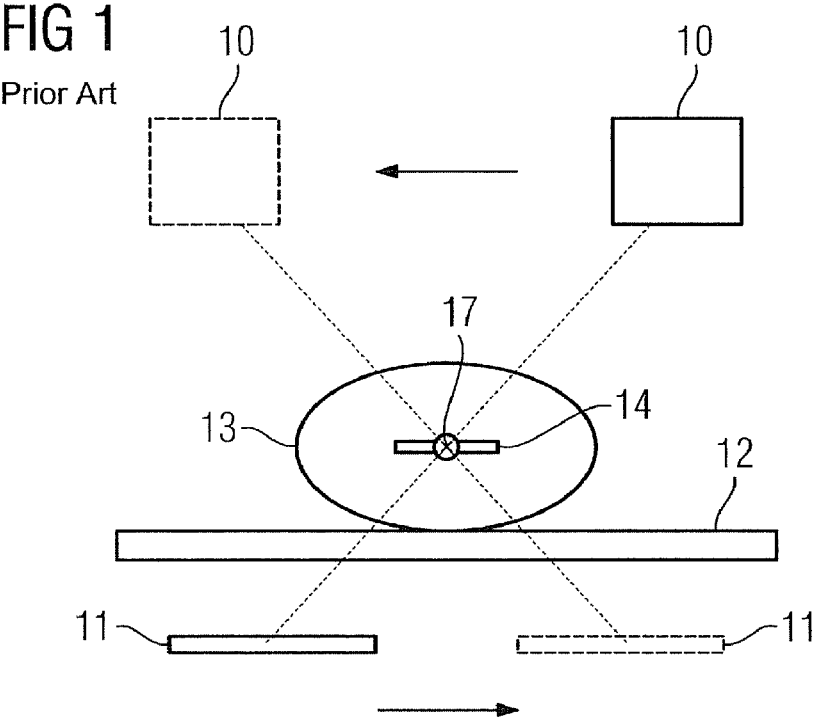
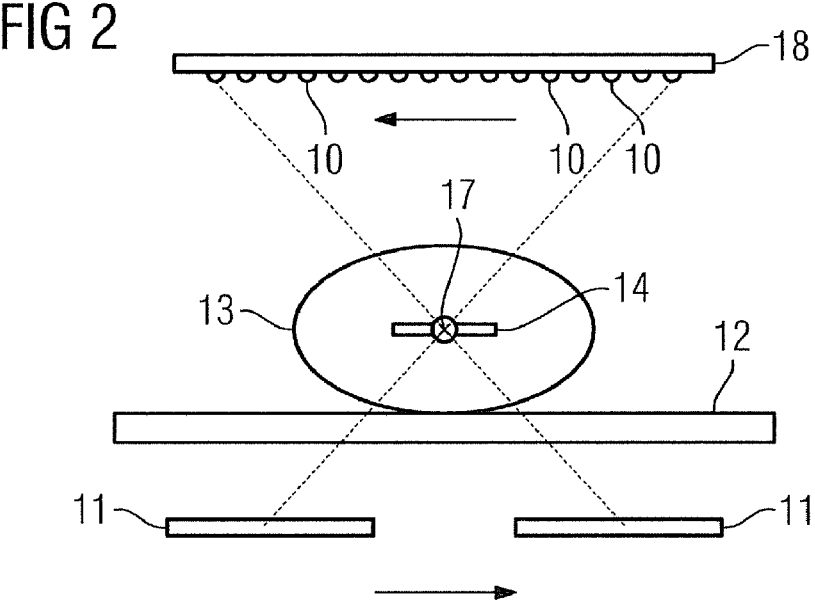

METHOD AND DEVICE FOR GENERATING A THREE-DIMENSIONAL X-RAY IMAGING

CROSS REFERENCE TO RELATED APPLICATIONS

This application claims priority of German application No. 10 2009 043 421.6 filed Sep. 29, 2009, which is incorporated by reference herein in its entirety.

FIELD OF THE INVENTION

The invention relates to a method for three-dimensional x-ray imaging as well as to a device for carrying out such a method.

BACKGROUND OF THE INVENTION

In order to obtain depth information of an object to be examined, what is referred to as tomography was developed as far back as the 1960s. Tomographs are images free from overlays of all object details lying in a particular slice. With a tomograph an x-ray source is moved in a first plane from a point "A" to a point "B", e.g. above the object to be examined, while an x-ray detector is moved below the object to be examined, for example in a plane parallel to the first plane, from point "B" to point "A". As a result of the movements the projections of all points of the irradiated object move in the image plane. Sharp images are only obtained of those object areas of which the projections are moving in the film plane at the same speed as the x-ray detector. The first solutions for tomography possessed a "tomo bar" with which a mechanical coupling between x-ray source and x-ray detector was achieved, modern solutions possess an electronic control which controls the motorized drive for x-ray source and x-ray detector.

Tomo synthesis represents a further development of tomography. In this system the images are not simply averaged during the movement but are recorded individually and then fed to a 3D reconstruction method. The advantage is that not only one individual slice but a number of parallel slices can be reconstructed. In addition the x-ray source can be moved in different scanning paths, such as ellipses, loops or spirals for example, with the scanning path always remaining in one plane however. A tomosynthesis system with a C-arm is known for example from DE 10 2007 037 996 A1.

3D x-ray imaging with this type of tomosynthesis system with a C-arm or with x-ray source and x-ray detector arranged mechanically independently of each other is far slower for example than computed tomography since a CT gantry can be rotated very quickly because of its mechanical properties.

SUMMARY OF THE INVENTION

The object of the present invention is to provide a tomosynthesis method which makes possible especially fast and easy recording of 3D images; the object of the invention is to provide an x-ray device suitable for carrying out the method.

The object is inventively achieved by a method for three-dimensional tomographic x-ray imaging and by a device in accordance with the independent claims. Advantageous embodiments of the invention are the subject matter of the associated dependant claims in each case.

With the method for three-dimensional tomographic x-ray imaging, tomosynthetic projection images are recorded from different recording angles along a tomosynthetic scanning path and three-dimensional image data is reconstructed from the tomosynthetic projection images, with a tomosynthetic x-ray device being used with a plurality of x-ray sources arranged at a distance from one on a holder, with each projection image being created in each case by means of a different x-ray source and the x-ray sources being fixed in their positions during the method. There is thus no mechanical movement on the part of the x-ray sources but instead the change of recording angle is solely effected by the activation of the x-ray sources one after the other. The inventive method enables fast, simple and effortless recording of projection images from a number of recording angles without a movement of the x-ray source. This makes a very fast recording time possible which is not restricted by mechanical movements but at most by the detector readout time. In this way new applications of real-time imaging such as tomographic fluoroscopy, real-time localization of interventional instruments and 4D angiography are possible.

To carry out the method a tomosynthetic x-ray device, featuring a holder with a plurality of x-ray sources arranged at a distance from one another and an x-ray detector are used, with the x-ray sources being arranged such that sequential activation of individual x-ray sources enables tomosynthetic projection images to be recorded from different recording angles along a tomosynthetic scanning path. The x-ray sources are thus arranged in a form which in known tomosynthetic methods is described by the scanning path of the single x-ray source. In particular the x-ray sources are all located in one plane. The x-ray sources are activated for the inventive method in accordance with a time sequence, with for example x-ray sources arranged next to one another being able to be activated directly after one another; during this process a projection image is then recorded in each case by means of the x-ray detector.

The x-ray sources are provided in accordance with one embodiment of the invention in an elliptical or circular or rectangular or spiral-shaped or linear arrangement, especially in a common plane. Accordingly the associated tomosynthetic scanning path is embodied elliptically or as a circle or a rectangle or a spiral or a line. The tomosynthetic scanning path can be closed or non-closed in such cases.

In accordance with a further embodiment of the invention the x-ray detector used for recording the projection images is moved during the method. The x-ray detector is for example synchronized with the activation of the x-ray sources in a plane parallel to the plane of the x-ray source arrangement. In this case the movement of the x-ray detector is such that the projections of the x-ray sources onto the x-ray detector at the time of their activation exhibit a common virtual fulcrum.

In accordance with a further embodiment of the invention the x-ray detector used to record the projection images is fixed in one position during the method. This is above all also advantageous if the x-ray sources or the x-ray detector are arranged on a common C-arm, since then no mechanical movement is necessary. The x-ray detector in this case is sufficiently large and is arranged such that a projection through the area of the object to be examined to be recorded or the fulcrum on the x-ray detector is possible from all x-ray sources to be activated.

In accordance with a further embodiment of the invention of the x-ray sources are formed by emission guns with field emission cathodes. Such field emission guns are especially small and light to manufacture. In accordance with a further embodiment of the invention the field emission cathodes are formed on the basis of carbon nano tubes so called CNT cathodes). These types of material exhibit an especially good emission characteristic but are also stable with high currents and can also be manufactured especially small. Field emission gins can also be activated especially quickly and generate no heat or little heat.

In an advantageous manner a further central x-ray source is arranged on the holder. Thus for example a C-arm x-ray system with a conventional x-ray source can be modified such that an arrangement of x-ray sources can be additionally attached to the C-arm. In this way both tomosynthesis in accordance with the inventive method and also conventional x-ray imaging is possible.

Expediently the x-ray sources and the x-ray detectors are arranged together on a C-arm.

In accordance with a further embodiment of the invention the tomosynthetic x-ray device is embodied as a biplanar x-ray device with a second holder with a plurality of x-ray sources arranged at a distance from one another and a second x-ray detector. The tomosynthetic x-ray device can for example feature two adjustable C-arms, on each of which a plurality of x-ray sources and an x-ray detector are arranged.

BRIEF DESCRIPTION OF THE DRAWINGS

The invention as well as further advantageous embodiment in accordance with features of the dependant claims will be explained below in greater detail with reference to schematically represented exemplary embodiments in the drawing, without the invention being restricted to these exemplary embodiments. The drawings show:

FIG. 1 a view of a tomography system in accordance with the prior art;

FIG. 2 a side view of an inventive tomosynthesis x-ray device;

DETAILED DESCRIPTION OF THE INVENTION

A known tomography or tomosynthetic x-ray device is shown in FIG. 1. An object to be examined 13 is arranged on a patient table 12. On one side of the object to be examined (above it in the case shown) is an x-ray emitter 10 and on the opposite side (below it in the case shown is arranged an x-ray detector 11, with a reversed arrangement being possible. X-ray source and x-ray detector are arranged such that a projection image of the object to be examined can be recorded. Subsequently the x-ray emitter and the object to be examined are moved in a so-called scanning path in a first plane parallel to the plane of the object to be examined, e.g. in a linear or circular scanning path. At the same time the x-ray detector is moved in a second plane parallel to the plane of the object to be examined and in parallel to the first plane, but such that projections of the x-ray limit on the x-ray detector pass through a common virtual fulcrum. At a plurality of points on the scanning path, i.e. for different recording angles of the x-ray emitter in relation to the central fulcrum, projection images are recorded. The projection images are reconstructed into 3D images of slices 14 of the object to be examined.

Figure 3:
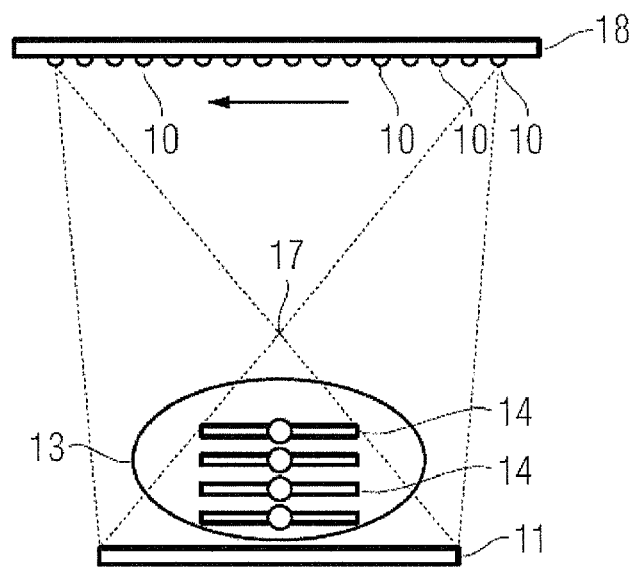
FIG. 3 a side view of a further inventive tomosynthetic x-ray device.
Figure 4:
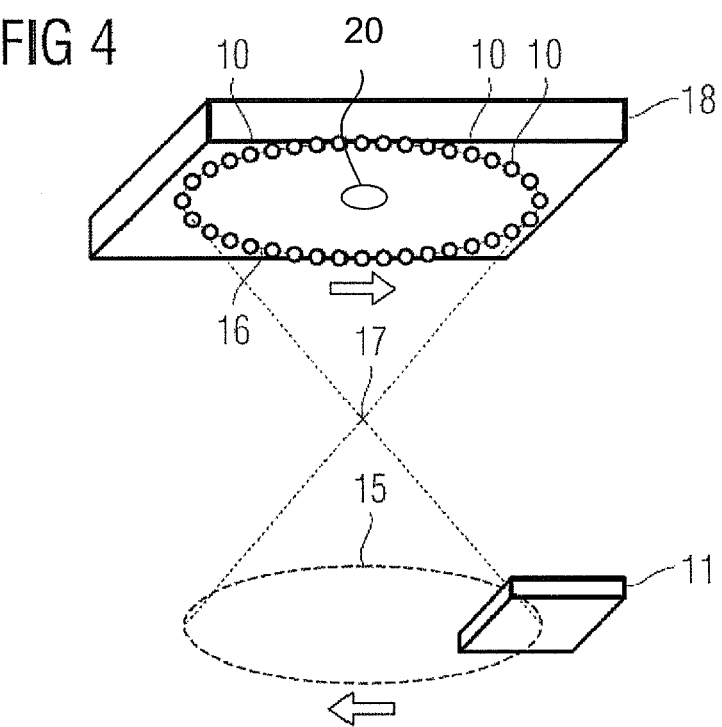
FIG. 4 a perspective view of an inventive tomosynthetic x-ray device.

The inventive method, by contrast with the known tomosynthetic method, is far faster and able to be carried out without mechanical movement. This allows a reconstructed 3D image to be obtained much more quickly and the wear on the mechanical components is much lower. The most important components of inventive tomosynthetic x-ray devices are shown in FIG. 2 to FIG. 4. A plurality of x-ray emitters 10 is arranged on a holder 18. In this embodiment the arrangement of x-ray emitters is preferably in one plane. The x-ray emitters can be provided in a linear arrangement as shown in FIG. 2 and FIG. 3, or in an elliptical arrangement as in FIG. 4, further arrangements such as circles, loops, spirals, L shapes in an n-angle shape or diamond shape are also possible. The scanning path is predetermined by the arrangement.

The x-ray emitters are especially formed by field emission guns which are embodied especially small, light and efficient. The field emission guns each have a field emission cathode for generating and transmitting electrons. With a field emission cathode electrons are emitted by applying a sufficiently high electrical field. Field emission cathodes allow a very high, well controlled and easily-focusable electron beam flow. The x-ray emitters can each be assigned collimators which form the x-ray beam generated by the respective x-ray emitters such that the x-ray beam is emitted in the desired direction.

In the inventive method, especially under the control of a system controller of the tomography x-ray device, the x-ray emitters arranged in the arrangement are activated one after the other to emit x-ray radiation and a projection image is recorded for each x-ray emitter in each case. The x-ray emitters in this case are especially activated in the order of their arrangement. For the linear arrangement in FIG. 2 or 3 the x-ray emitter located at the beginning of the arrangement is activated as the first emitter then in the second, arranged next to it, then the third x-ray emitter etc. up to the last x-ray emitter of the linear arrangement. Synchronously with the activation of the x-ray emitters, in accordance with the first alternative—shown in FIG. 2—the x-ray detector 11 is moved in the opposite direction of the activation of the x-ray emitters in the parallel to the x-ray emitter arrangement. The movement is matched to the activation of the x-ray emitters such that, for each activation a projection image can be recorded and read out. Ideally the connecting line between the respective focus of the activated x-ray emitter and the center point of the x-ray detector intersects the fulcrum 17 at the time that the projection image is recorded.

In accordance with a second alternative—shown in FIG. 3—the x-ray detector is embodied sufficiently large to ensure that the x-ray beam of each possible x-ray emitter still arrives at the x-ray detector after passing through the fulcrum. In the method the x-ray emitters are activated in turn as described above and projection images are recorded, with only a part of the x-ray detector being irradiated here for each projection image.

An elliptical arrangement of the x-ray emitters is shown in FIG. 4, accordingly the scanning path 16, and if the x-ray detector moves, its movement path 15, are likewise elliptical. For an elliptical and more generally for a closed arrangement of the x-ray emitters, one x-ray unit (in general any given emitter) is first activated, subsequently in turn the respective x-ray emitter arranged on one side next to it, until each x-ray emitter has been activated once and projection images from all x-ray emitters are available.

From the projection images recorded slices 14 of the object to be examined can be reconstructed in the known way by means of an image processing unit or a data-processing unit with corresponding software and thereby a 3D image created. The slices or the 3D image can subsequently be shown on a display unit.

The inventive tomosynthesis x-ray device can also be embodied as a modified angiography system in which, in addition to a first main x-ray source 20 (FIG. 4), an arrangement with the plurality of x-ray sources as described above is also present. The main x-ray source in this case is arranged together with an x-ray detector on a C-arm, the plurality of x-ray sources in an arrangement as described (linear, elliptical, spiral-shaped etc.) next to each other or around the main x-ray source with or without additional support. In this way alternative imaging with the main x-ray source (e.g. angiography imaging) or with the arrangement of x-ray sources (e.g. tomosynthesis) can be carried out. Angiography is especially used for 3D images of heart and blood vessels as well as for monitoring minimally-invasive interventions. An angiography system can for example feature a see-arm supported movably on an articulated arm robot with a field emission radiator and a flat panel detector, with the C-arm being embodied so that it can be moved by the articulated arm robot to any given translations and rotations and especially for recording a plurality of projection images during a rotation around an object to be examined, with the projection images subsequently able to be reconstructed into a 3D image.

A biplanar system with, two C-arms for example, can also be provided, with a plurality of x-ray sources being arranged in a corresponding arrangement (e.g. field emission guns) and an x-ray detector. A biplanar system is also possible in which a main x-ray source as well as a plurality of further x-ray sources are provided in a corresponding arrangement on each C-arm.

An inventive tomosynthetic x-ray device or a combined angiography-tomosynthetic x-ray device, in addition to tomosynthesis, enables the following applications to be carried out for example:

Tomographic real-time fluoroscopy: Tomosynthetic reconstruction of 3D projection images and immediate display of the reconstructed data obtained in a rapid sequence, e.g. in slices or as volume rendering. This can for example be used for process control of embolizations.

Real-time compensation for patient movements by 2D/3D or 3D/3D registration of the image data of the plurality of x-ray sources with previously recorded 3D rotation angiography image data, Real-time localization of interventional instruments, 4D angiography: Reconstruction of time series by means of tomosynthesis for dynamic reconstruction of blood vessels, 4D angiography with evaluation of time curves: Reconstruction of time series by means of tomosynthesis for controlling the treatment of stenoses, usable for assessing the blood flow in blood vessels, Dynamic perfusion imaging: Reconstruction of time series by means of tomosynthesis for following the dynamics of a contrast media injection for determining functional tissue parameters, Tomosynthetic temperature imaging: Sequential 3D volumes are recorded by means of tomosynthesis during a thermal therapy (e.g. RF ablation) in order to reconstruct the dynamic temperature distribution from these.

Real-time stereo fluoroscopy: By activating two tubes in each case stereo image pairs can be recorded without mechanical movement of the x-ray tubes.

Within the framework of the invention the x-ray sources, for example the field emission radiators, of the arrangement are activated synchronized in time in each case with the movement of the x-ray detector, while the x-ray detector is moving below the patient linearly for example. The movement of the x-ray detector and the synchronized activation of the x-ray sources causes linear slice images to be created. In a further alternative a sufficiently large x-ray detector can also remain static. Any given slices of the area to be examined which are irradiated by all x-ray sources can then be reconstructed.

The invention can be briefly summarized as follows: For an especially fast and simple 3D imaging a method is provided for three-dimensional tomographic x-ray imaging is provided in which tomosynthetic projection images are recorded from different recording angles along a tomosynthetic scanning path and three-dimensional image data is reconstructed from the tomosynthetic projection images, with a tomosynthetic x-ray device with a plurality of x-ray sources spaced at a distance from each other on a holder being used, with each projection image in each case being created by a different x-ray source and the x-ray sources being fixed in the same place during the method.

The invention claimed is:

1. A method for generating a three-dimensional x-ray tomosynthetic imaging of an object in combination with an alternative non-tomosynthetic x-ray imaging of the object, comprising:
   recording a plurality of tomosynthetic projection images of the object from different recording angles along a tomosynthetic scanning path by a tomosynthetic x-ray device comprising an x-ray detector and a plurality of tomosynthetic x-ray sources arranged on a holder at a distance from one another;
   disposing on the holder having the tomosynthetic x-ray sources a further x-ray source to provide the alternative x-ray imaging of the object;
   reconstructing the three-dimensional x-ray imaging from the tomosynthetic projection images; and
   acquiring and processing signals from the further x-ray source to provide the alternative non-tomosynthetic imaging of the object;
   wherein each of the tomosynthetic projection images is recorded by a different x-ray source of the plurality of tomosynthetic x-ray sources and the plurality of tomosynthetic x-ray sources remain in same position during recording the tomosynthetic projection images.

2. The method as claimed in claim 1, wherein the tomosynthetic projection images are recorded by consecutively and individually activating the x-ray sources.

3. The method as claimed in claim 1, wherein the x-ray detector moves during recording the tomosynthetic projection images.

4. The method as claimed in claim 1, wherein the x-ray detector remains statically during recording the tomosynthetic projection images.

5. The method as claimed in claim 1, wherein the tomosynthetic scanning path is a closed loop.

6. The method as claimed in claim 5, wherein the closed loop comprises a circle, an ellipse, or a rectangle.

7. The method as claimed in claim 1, wherein the tomosynthetic scanning path is a non-closed path.

8. The method as claimed in claim 7, wherein the non-closed path comprises a spiral or a line.

9. An x-ray device for generating a three-dimensional tomosynthetic x-ray imaging of an object in combination with an alternative non-tomosynthetic x-ray imaging of the object, comprising:
   a first holder;
   a plurality of tomosynthetic x-ray sources arranged on the holder at a distance from one another for emitting x-ray beams;

a further x-ray source disposed on the holder having the tomosynthetic x-ray sources, the further x-ray source arranged to provide the alternative x-ray imaging of the object; and an x-ray detector for recording a plurality of tomosynthetic projection images of the object from different recording angles along a tomosynthetic scanning path in order to reconstruct the three-dimensional x-ray imaging, wherein the plurality of tomosynthetic x-ray sources are configured to be consecutively and individually activated and remain in same position during recording the tomosynthetic projection images, wherein signals from the further x-ray source are acquired and processed to provide the alternative non-tomosynthetic imaging of the object.

10. The tomosynthetic x-ray device as claimed in claim 9, wherein the x-ray sources are arranged in a shape of a circular, an ellipse, a rectangular, a spiral, or a line.

11. The tomosynthetic x-ray device as claimed in claim 9, wherein the x-ray sources comprise emission guns with field emission cathodes.

12. The tomosynthetic x-ray device as claimed in claim 11, wherein the field emission guns comprise a nano-structured material with carbon nano tubes.

13. The tomosynthetic x-ray device as claimed in claim 9, wherein the x-ray sources and the x-ray detector are arranged together on a C-arm.

14. The tomosynthetic x-ray device as claimed in claim 9, wherein the tomosynthetic x-ray device is a biplane x-ray device comprising:
a first C-arm to support the first holder on a first plane;
a second holder,
a second C-arm to support the second holder on a second plane different than the first plane;
a plurality of second set of tomosynthetic x-ray sources arranged on the second holder at a distance from one another;
a second further x-ray source disposed on the second holder having the second set of tomosynthetic x-ray sources, the second further x-ray source arranged to provide further alternative x-ray non-tomosynthetic imaging of the object; and
a second x-ray detector.

* * * * *